United States Patent
Upadhyayula et al.

(10) Patent No.: US 8,484,044 B2
(45) Date of Patent: Jul. 9, 2013

(54) SERVICE IDENTIFICATION AND DECOMPOSITION FOR A HEALTH CARE ENTERPRISE

(75) Inventors: Prakash Upadhyayula, Plainfield, IL (US); Harshwinder Singh, North Wales, PA (US); Kari Brey, Andover, MN (US)

(73) Assignee: Aetna Inc., Hartford, CT (US)

( * ) Notice: Subject to any disclaimer, the term of this patent is extended or adjusted under 35 U.S.C. 154(b) by 1006 days.

(21) Appl. No.: 12/031,371

(22) Filed: Feb. 14, 2008

(65) Prior Publication Data

US 2009/0210499 A1  Aug. 20, 2009

(51) Int. Cl.
*G06Q 10/00* (2012.01)
*G06Q 50/00* (2012.01)

(52) U.S. Cl.
USPC .......... 705/2; 705/3; 705/4; 370/351

(58) Field of Classification Search
USPC .......... 705/2–4; 370/351
See application file for complete search history.

(56) References Cited

U.S. PATENT DOCUMENTS

| | | | |
|---|---|---|---|
| 6,073,106 A | 6/2000 | Rozen et al. | |
| 6,138,122 A | 10/2000 | Smith et al. | |
| 6,336,138 B1 | 1/2002 | Caswell et al. | |
| 2002/0128879 A1 | 9/2002 | Spears | |
| 2006/0069717 A1* | 3/2006 | Mamou et al. | 709/203 |
| 2007/0027714 A1 | 2/2007 | Fenno | |
| 2007/0185793 A1 | 8/2007 | George | |
| 2007/0208596 A1 | 9/2007 | Meiner et al. | |
| 2007/0226007 A1 | 9/2007 | Osaki et al. | |
| 2008/0244594 A1* | 10/2008 | Chen et al. | 718/104 |
| 2009/0080408 A1* | 3/2009 | Natoli et al. | 370/351 |

* cited by examiner

*Primary Examiner* — Luke Gilligan
(74) *Attorney, Agent, or Firm* — Leydig, Voit & Mayer, Ltd.

(57) ABSTRACT

In embodiments, a health insurance computer application enterprise system is provided employing a service oriented architecture (SOA) with a service granularity component that dynamically customizes a reusable service based on one or more of user identity element, service data elements, and service action elements parsed from service request parameters. The health insurance enterprise system includes a plurality of applications making use of functionality provided by a reusable service. In an embodiment, the health insurance enterprise system includes a customer service application, a consumer web portal application, and an integrated voice response (IVR) application. The applications provide different channels of communicating health insurance data to various health insurance system constituents by presenting customized views of the data tailored to a given communications method, user access rights, as well as other factors.

17 Claims, 3 Drawing Sheets

SERVICE IDENTIFICATION AND DECOMPOSITION FOR A HEALTH CARE ENTERPRISE

FIELD OF THE INVENTION

This invention relates generally to the field of enterprise management and more specifically to the area of computer application integration.

BACKGROUND OF THE INVENTION

Service Oriented Architecture (SOA) is a computer application integration architecture that is based on a concept of an application service. An application service (hereinafter "service") typically encapsulates a business function, such as processing of supplied data in accordance with a predetermined business process, and provides platform independent functionality between heterogeneous applications. The service functionality is specified via an implementation independent service interface definition, such as a Web Services Description Language (WSDL). As an example of a service, a thin client application implemented on a JavaScript, Java and/or other platform requests user authentication and supplies user credentials to an authentication service executed by one or more server applications implemented on a COBOL platform. Thus, the service may be provided by one or more service provider applications that process the service request in accordance with their specific technology implementation and provide the results of the service execution back to a service consumer application per service definition. The service consumer application, in turn, may be implemented on a technology platform that is different from the service provider application. The service consumer and service provider applications are loosely coupled through the service interface while hiding the implementation details.

While SOA implementations integrate a number of heterogeneous applications, typical enterprise system development timelines drive tactical architectural decisions that result in creation of multiple dedicated services which are specific to a given application environment. In particular, health care enterprises, such as health insurance enterprises, integrate a multitude of heterogeneous application environments to accommodate numerous communication channels necessary for the flow of health care data. Although similar type of information may be processed by various applications and services within a health care enterprise, each application environment typically employs its own dedicated set of services due to requiring a different level of detail, or granularity, for the data supplied to and processed by its respective set of services. Thus, multiple services are created for processing similar information, which decreases the overall system efficiency, increases development, maintenance and computational costs, and negatively affects system performance.

BRIEF SUMMARY OF THE INVENTION

Embodiments of the invention are used to provide a health insurance computer application enterprise system employing a service oriented architecture (SOA) with a service granularity component that dynamically customizes a reusable service based on one or more of user identity (i.e., "who") element, common service data (i.e., "what info") elements, and common service action (i.e., "what action") elements parsed from service request parameters. The health insurance enterprise system includes a plurality of computer systems and applications making use of functionality provided by a reusable service, such as by exchanging service request and service response messages with the service granularity component via a network. In an embodiment, the health insurance enterprise system includes a customer service application, a consumer web portal application, and an integrated voice response (IVR) application. The applications provide different channels of communicating health insurance data to various health insurance system constituents by presenting customized views of the data tailored to a given communications method, user access rights (e.g., display versus editing of member data), as well as other factors.

Therefore, to provide a claim view of member data, each enterprise application initiates a service request that includes parameters corresponding to the requested data and/or the actions that need to be performed using requested or collected data, as well as user's identity. Based on the parameterized request, the granularity component identifies a reusable service for supplying the requested data elements and/or performing requested processing. In one embodiment, the reusable service is capable of delivering a plurality of data elements (e.g., various claim details), while the granularity component parses the service request to customize the reusable service in accordance with a particular subset of data required by the requesting application. For example, a service request for displaying claims detail originating from a customer service application will request information corresponding to claim codes (e.g., CPT codes), as well as editable fields for input of customer service representative (CSR) notes (in accordance with CSR's user permissions level), while claim view service requests from consumer web portal and/or IVR application will only require most recent claim detail devoid of claim codes and editable fields. Similarly, the granularity component customizes the reusable service in accordance with types of requested actions. For example, a customer service application may require that claim data is sorted by date and then by claim code, while consumer portal requires claim data sorted only by date. In an embodiment, the granularity component customizes the reusable service into a plurality of services providing some or all of the functionality of the reusable service depending on the calling application request parameters, but all conforming to the service definition of the reusable service and, therefore, providing consistent information across all channels of the computer enterprise.

When the service messages are relayed via a service bus having a specific message format, the granularity component transforms the format of service request and service response messages, for example to conform to the message format of the service bus.

In one aspect of the invention, a health care enterprise computer system is provided comprising a plurality of health care applications for communicating health care information across the enterprise via a service oriented architecture, a granularity component for dynamically customizing a reusable service within the service oriented architecture, the reusable service delivering the health care information to the plurality of health care applications, and wherein the granularity component customizes the reusable service for each of the plurality of health care applications based on service request parameters comprising one or more of user identification fields, requested data fields, and requested action fields.

In another aspect of the invention, in a service oriented architecture for a health care enterprise computer system, a method is provided for providing a reusable service to a plurality of health care applications, the method comprising receiving a service request from at least one of the plurality of health care applications, parsing the service request to identify one or more of user identification fields, requested data fields, and requested action fields, dynamically customizing the reusable service for the at least on of the plurality of health care applications based on one or more of the parsed service request fields, and invoking the customized reusable service.

In yet another aspect of the invention, in a service oriented architecture for a health care enterprise computer system, a computer readable medium is provided having stored thereon computer executable instructions for providing a reusable service to a plurality of health care applications, the instructions comprising receiving a service request from at least one of the plurality of health care applications, parsing the service request to identify one or more of user identification fields, requested data fields, and requested action fields, dynamically customizing the reusable service for the at least on of the plurality of health care applications based on one or more of the parsed service request fields, and invoking the customized reusable service.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

The following examples further illustrate the invention but, of course, should not be construed as in any way limiting its scope.

Figure 1:
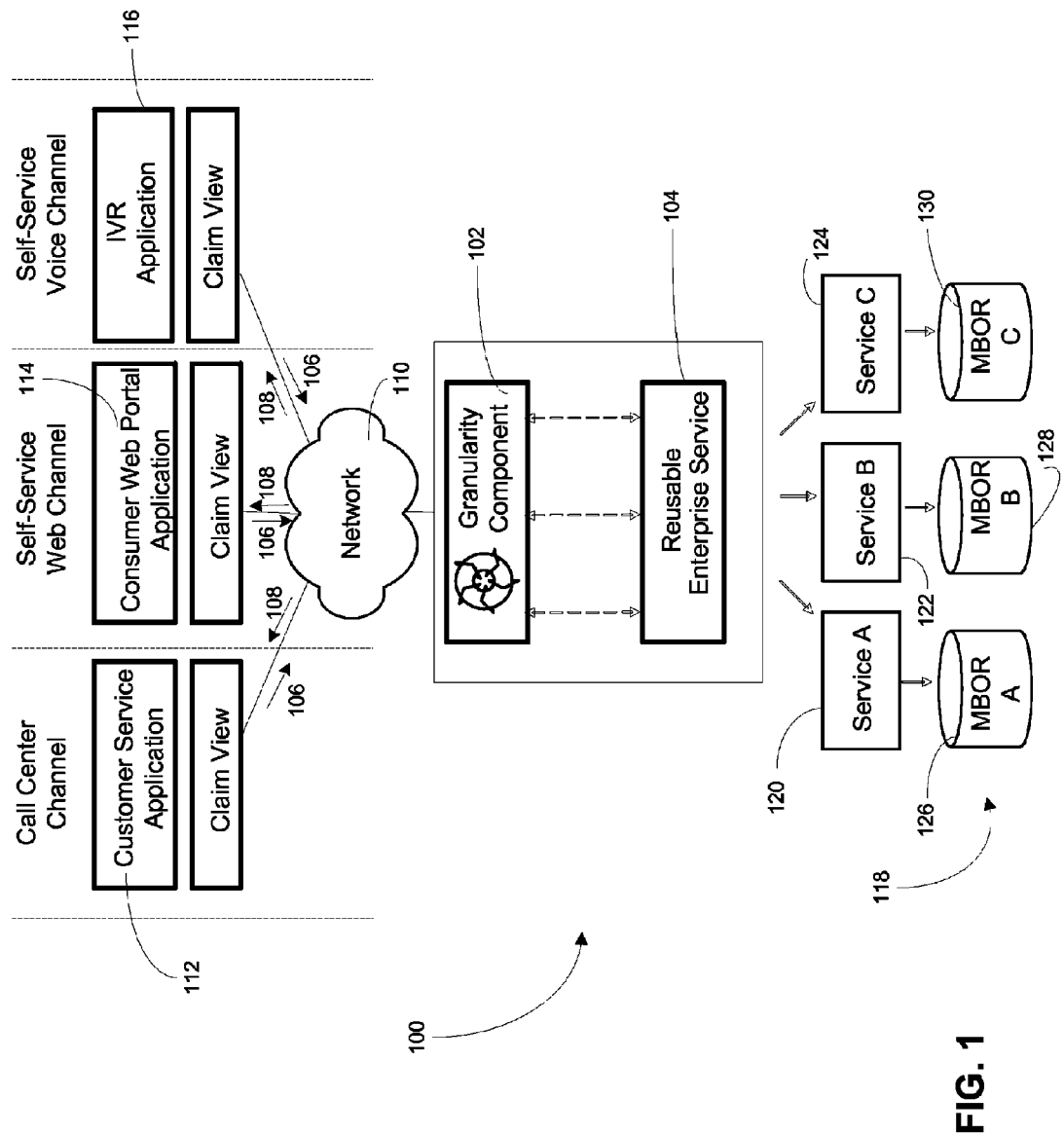
FIG. 1 is a diagram of a health insurance enterprise system employing a service oriented architecture (SOA) with a service granularity component that dynamically customizes a reusable service, as contemplated by an embodiment of the present invention.

Turning to FIG. 1, an implementation of a system contemplated by an embodiment of the invention is shown with respect to a health insurance computer application enterprise system 100 employing a service oriented architecture (SOA) with a service granularity component 102 that dynamically customizes a reusable service 104 based on one or more of user identity (i.e., "who") element, common service data (i.e., "what info") elements, and common service action (i.e., "what action") elements parsed from service request parameters.

The health insurance enterprise system 100 includes a plurality of computer systems and applications making use of functionality provided by a reusable service 104, such as by exchanging service request and service response messages 106, 108 with the service granularity component 102 via a network 110. In embodiments, the network 110 is a local area network (LAN), a wide area network (WAN), and the Internet. In the illustrated embodiment, the health insurance enterprise system 100 includes a customer service application 112, a consumer web portal application 114, and an integrated voice response (IVR) application 116. The applications 112-116 provide different channels of communicating health insurance data 118 to various health insurance system constituents by presenting customized views of the data 118 tailored to a given communications method, user access rights (e.g., display versus editing of member data), as well as other factors. For example, a customer service representative (CSR) uses the customer service application 112, such as a thick client or a web browser, to access the health insurance data 118 via a LAN or intranet connection, while a health plan member has an option to access the data 118 via a browser-based web portal 114 or by receiving audible feedback from an IVR application 116 during a telephone session. The customer service representative is capable of interpreting claim description and CPT claim code data for investigating and verifying claim processing and, therefore, can see greater claim processing detail than a health plan member who is presented with a streamlined interface for ease of use. Furthermore, a customer service representative has the ability to edit the data 118, such as by appending notes with regard to member phone calls. In addition to claims data, the customer service application 112 provides a customer service representative with a view of plan benefit data for answering member questions regarding covered procedures and covered dependents, accepting input for authorizing covered treatment, updating dependent eligibility status, and the like. While the consumer web portal application 114 and the IVR application 116 also relay plan benefits data and covered dependent information to the health plan member, they do not permit a user to preauthorize treatment, update eligibility status, or edit data.

Therefore, to provide a claim view of member data 118, each enterprise application 112-116 initiates a service request 106 that includes parameters corresponding to the requested data 118 and/or the actions that need to be performed using requested or collected data, as well as user's identity (e.g., user id of a CSR or member id of the health plan member). For example, the service request 106 may include a request for one or more of member's first name, last name, date of birth, insurance id number, claim number, date of claimed service, and other member data 118, as well as a request to sort or otherwise manipulate requested data (e.g., calculate eligible claim period based on the date of claimed service). Based on the parameterized request 106, the granularity component 102 identifies a reusable service 104 for supplying the requested data elements and/or performing requested processing. The granularity component 102 comprises computer executable instructions stored and executed in memory of one or more computers comprising the health insurance enterprise system 100. Preferably, the granularity component 102 resides on one or more server computers of the health insurance enterprise system 100.

In an embodiment, the reusable service 104 is capable of delivering a plurality of data elements (e.g., various claim details), while the granularity component 102 parses the service request 106 to customize the reusable service 104 in accordance with a particular subset of data required by the requesting application. For example, a service request for displaying claims detail originating from a customer service application 112 will request information corresponding to claim codes (e.g., CPT codes), as well as editable fields for input of CSR notes (in accordance with CSR's user permissions level), while claim view service requests from consumer web portal 114 and/or IVR application 116 will only require most recent claim detail devoid of claim codes and editable fields. Similarly, the granularity component 102 customizes the reusable service 104 in accordance with types of requested actions. For example, a customer service application may require that claim data is sorted by date and then by claim code, while consumer portal 114 requires claim data sorted only by date. In an embodiment, the granularity component 102 customizes the reusable service 104 into a plurality of services 120-124 providing some or all of the functionality of the reusable service 104 depending on the calling application request parameters, but all conforming to the service definition of the reusable service 104 and, therefore, providing consistent information across all channels of the computer enterprise 100.

When calling applications 112-116 require claim data from different sources, such as from different member book of records (MBOR) 126-130, the granularity component 102 invokes the customized services 120-124 accordingly. MBORs 126-130 may be separate claim databases including varying levels of claim detail required by the calling applications 112-116. Alternatively, MBORs 126-130 may be different tables comprising a single health insurance database.

In embodiments, service messaging is provided via SOAP over HTTP, Java Message Queue, or another transport protocol, such as Messaging Queues, that is compatible with applications 112-116, including SOA-enabled applications. When the service messages 106, 108 are relayed via a service bus having a specific message format, the granularity component 102 transforms the format of service request and service response messages 106, 108, for example to conform to the message format of the service bus.

Figure 2:
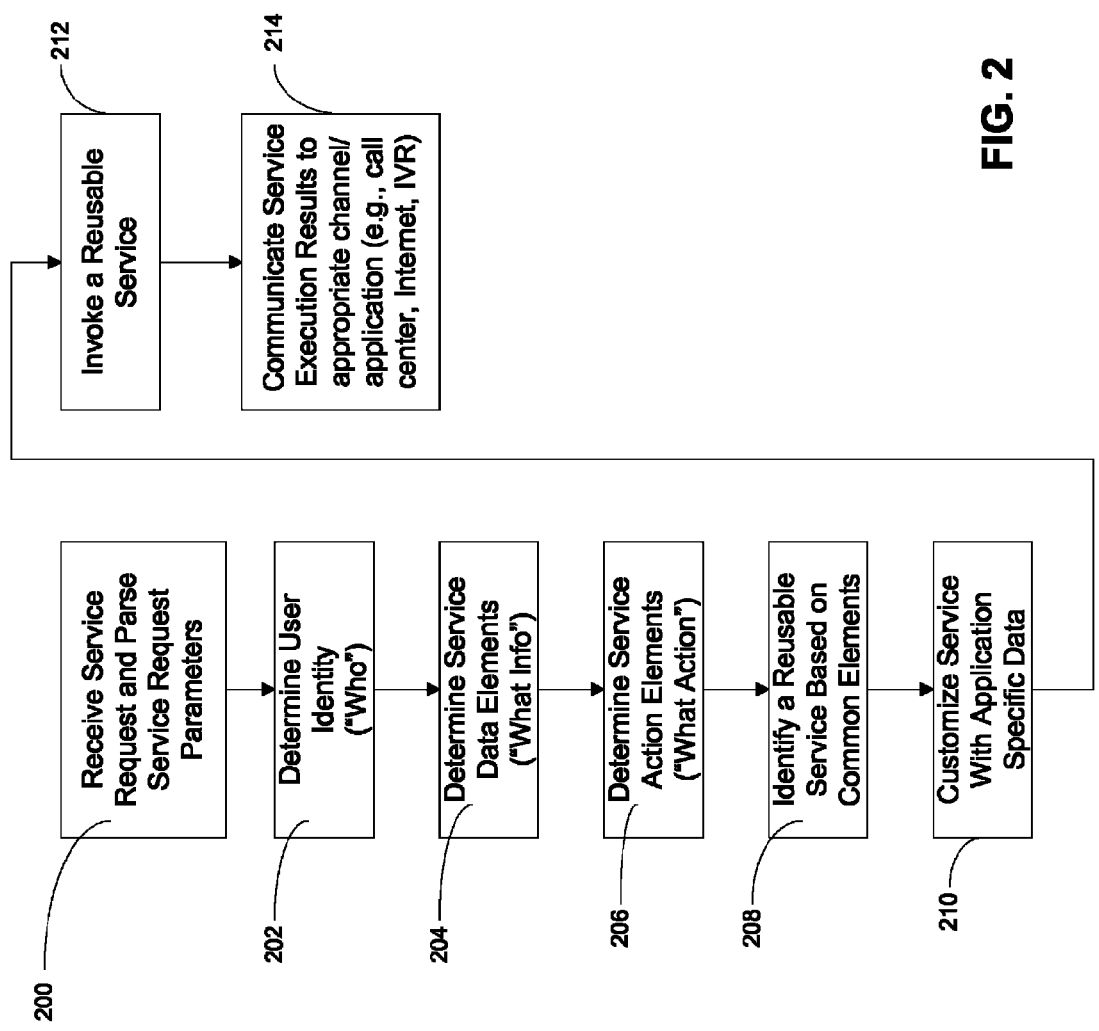
FIG. 2 is a flow chart illustrating a method for dynamically customizing a reusable service of FIG. 1 based on one or more of a user identity (i.e., "who") element, common service data (i.e., "what info") elements, and common service action (i.e., "what action") elements, as contemplated by an embodiment of the present invention.

Turning to FIG. 2, an embodiment of a method for dynamically customizing a reusable service based on one or more of a user identity (i.e., "who") element, common service data (i.e., "what info") elements, and common service action (i.e., "what action") elements is illustrated. In step 200, the granularity component 102 receives a service request (e.g., by way of a service request message 106) and parses the service request parameters. Next, the granularity component determines the user's identity, as well as service data (e.g., claims, CPT codes) and service action elements associated with the request, steps 204-206. In step 208, the granularity component 102 identifies a reusable service 104 by matching the one or more of the user, action, and service data categories with a list of available reusable services that provide the requested functionality. In an embodiment, reusable service 104 is discoverable among a predetermined listed of services. The predetermined list of services is, preferably, a fixed list where a called service is aware of the calling service in order to invoke the reusable service 104 with appropriate security permissions. For instance, when a consumer web portal application 114 requests claim data, the granularity component 102 identifies a service 104 that delivers claim data and, possibly, additional data, such as CPT codes. Alternatively, each of the plurality of applications 112-116 is associated with one or more predetermined reusable services 104 ahead of time.

Next, in step 210, the granularity component customizes the identified reusable service 104 with application-specific data (e.g., based on user identity and/or requested data or actions). In the above example, only basic claim detail is requested because the consumer web portal 114 is not able to display CPT codes. In steps 212, 214, the granularity component 102 invokes a customized version of the reusable service 104 and communicates service execution results back to the calling application.

Figure 3:
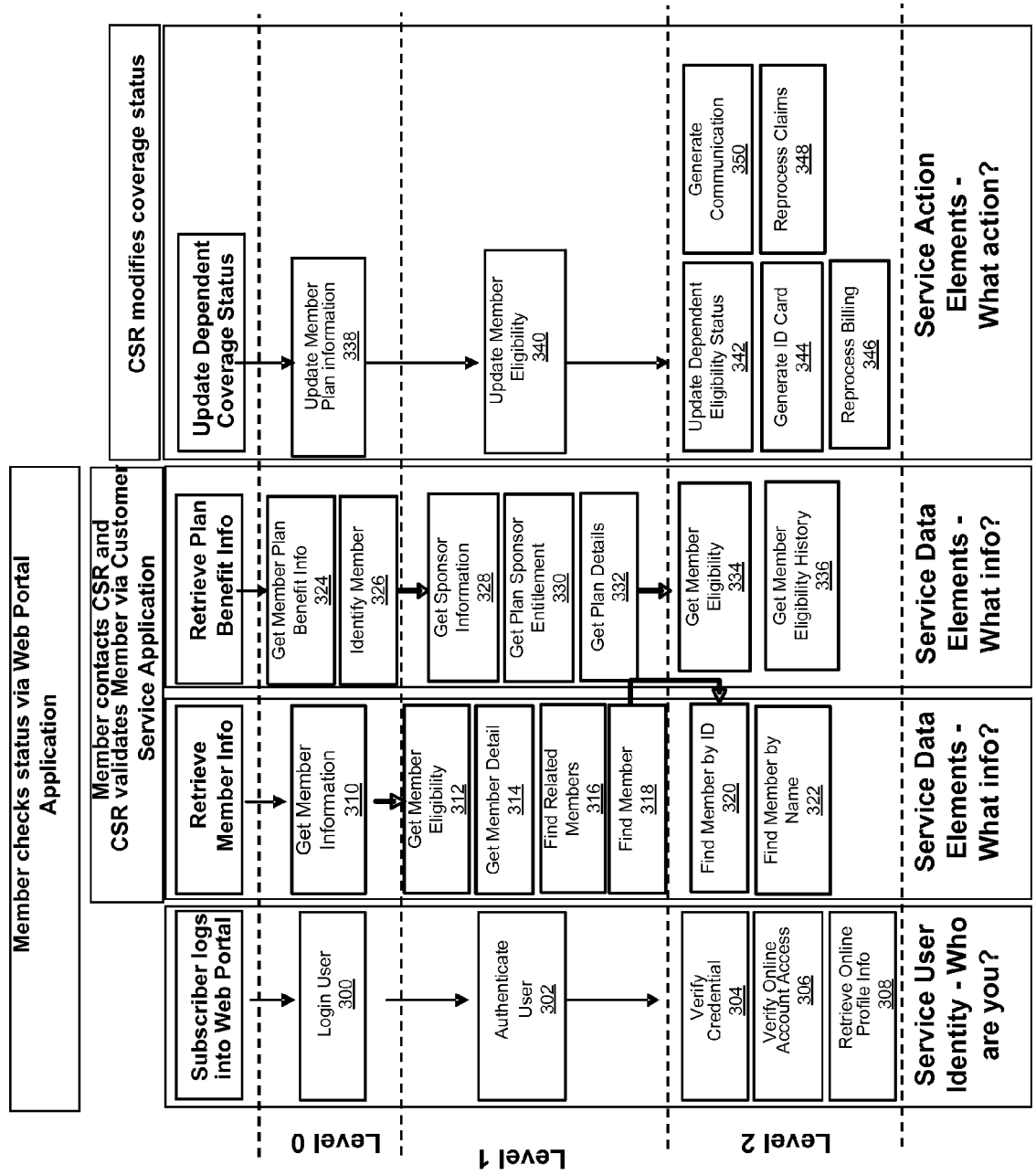
FIG. 3 is a service diagram illustrating an information flow during a health plan member's exemplary interaction with a customer service representative, in accordance with an embodiment of the invention.

Turning to FIG. 3, an embodiment of a service diagram representing an information flow during a health plan member's exemplary interaction with a customer service representative, is illustrated. In the exemplary scenario, a health insurance organization sends a letter to a health plan member notifying the member that a dependent will be removed from coverage upon turning eighteen years of age, unless the member submits proof of dependent's student status within a predetermined deadline. After the deadline, the member's dependent visits a physician, who submits a claim for rendered services. Since the member did not submit the requested proof of student status, the claim is rejected. When the member logs into the web portal application 114 to check the coverage status for the dependent, the web portal application 114 requests a plurality of services 300-308 to process the login request. In this embodiment, the login services 300-308 are specific to the web portal application 112 because the login functionality is particular to each application.

However, both web portal application 114 and the customer service application 112 require similar data in order to obtain member information, such as eligibility status and a list of covered dependents, as well as to display the member's plan benefit detail to ascertain covered services. Therefore, the service granularity component 102 identifies reusable services 310-336 for delivery of the shared data between the call center and self-service web channels. If one of the applications 112, 114 needs additional information, the granularity component 102 further customizes a corresponding reusable service with additional data elements.

Specifically, to retrieve member information, both applications 112, 114 request a Get Member Information reusable service 310, which returns member's coverage eligibility status (e.g., "covered" or "not covered"), as well as member's demographic and claim history detail, by invoking Get Member Eligibility and Get Member Detail reusable services 312, 314 respectively. To display demographic and claim history details for the member's dependents, the Get Member Detail reusable service 314 calls a Find Related Members reusable service 316. The Find Related Member service 316 is capable of finding related members via the Find Member reusable service 318, which finds a given member by member id or name by way of invoking a Find Member by ID reusable service 320 or Find Member by Name reusable service 322, respectively. The Find Member by Name service 322 includes multiple levels of granularity by accepting input of one or more of member's name, zip code, and address.

To display the member's plan benefit detail, the applications 112, 114 request execution of a reusable service Get Member Plan Benefit Info 324, which identifies the member via the Identify Member reusable service 326 and displays health plan sponsor, plan sponsor entitlement, and member's health plan benefit details via Get Sponsor Information, Get Plan Sponsor Entitlement, and Get Plan Details reusable services 328-332, respectively. Coverage eligibility status and eligibility update history for the member and his or her dependents is displayed via Get Member eligibility and Get Member Eligibility History reusable services 334, 336, respectively.

When the member and benefit information requested from the reusable services 310-336 is delivered back to the consumer web portal 114 and customer service application 112, the member ascertains that the dependent student's eligibility status changed from "covered" to "not covered." When the member contacts the CSR through a call center channel, the CSR verifies the eligibility status change by locating the member and dependent benefit information in the appropriate MBOR 126-130 after prompting the member for identification tokens, such as date of birth (DOB), member id, ZIP code, and/or address information. After identifying that a service request 106 originated from a customer service representative (e.g., by parsing user id), the granularity component 102 retrieves additional detail associated with the status change transaction (e.g., date of change, initials of person authorizing the change, associated notes, etc) for display to the CSR through Get Member Eligibility History service 336.

Finally, when the member submits proof of dependent's student status, the CSR updates the dependent's coverage eligibility status via the customer service application 112 by invoking an Update Member Plan Information individual service 338, which, in turn, triggers an Update Member Eligibility service 340 and Update Dependent Eligibility Status service 342 for updating the dependent's status to "covered." Dependent's coverage status update also triggers a plurality of individual services 344-350 for generating a new id card, reprocessing impacted claims and billing, and generating a communication (e.g., letter and/or email) to the member to notify of the coverage eligibility changes of the dependent.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A health care enterprise computer system, comprising:
    a plurality of health care applications hosted on one or more computers in a health care enterprise computer system for communicating health care information across the enterprise via a service oriented computing architecture; and
    a granularity component embodied on the one or more computers for dynamically customizing a reusable service within the service oriented computing architecture, wherein the reusable service delivers the health care information to the plurality of health care applications, the granularity component being configured to customize the reusable service for each of the plurality of health care applications based on service request parameters comprising one or more of user identification fields, requested data fields, and requested action fields and to return a result from the reusable service to at least one of the plurality of health care applications,
    wherein the reusable service comprises a service for retrieving health insurance plan member information.

2. The system of claim 1 wherein the granularity component is configured to transform a message format of the reusable service to a different service message format.

3. The system of claim 1 wherein said each of the plurality of health care applications is selected from the group consisting of a customer service application, a consumer web portal application, and an integrated voice response application.

4. The system of claim 1 wherein the reusable service is decomposed into one or more reusable services for obtaining a member's coverage eligibility status, obtaining the member's health insurance claim detail, and finding one or more other members related to the member.

5. The system of claim 4 wherein the reusable service for finding one or more other members related to the member includes multiple levels of granularity by accepting input of one or more of member's name, zip code, and address.

6. The system of claim 1 wherein the reusable service comprises a service for retrieving health insurance plan member's health plan benefit information.

7. The system of claim 6 wherein the reusable service is decomposed into one or more reusable services for identifying the member, getting health plan sponsor information, getting health plan sponsor entitlement information, getting health plan details, getting member coverage eligibility, and getting history of member coverage eligibility updates.

8. In a service oriented architecture embodied on one or more computers for a health care enterprise computer system, a computer-implemented method for providing a reusable service to a plurality of health care applications, the method comprising:
    receiving at the health care enterprise computer system, a service request from at least one of the plurality of health care applications;
    parsing the service request using the health care enterprise computer system to identify one or more of user identification fields, requested data fields, and requested action fields;
    dynamically customizing the reusable service, using the health care enterprise computer system, for the at least one of the plurality of health care applications based on one or more of the parsed service request fields;
    invoking the customized reusable service; and
    communicating a result from the customized reusable service to at least one of the plurality of health care applications,
    wherein the reusable service comprises a service for retrieving health insurance plan member information.

9. The method of claim 8 further comprising transforming a message format of the reusable service to a different service message format.

10. The method of claim 8 wherein said at least one of the plurality of health care applications is selected from the group consisting of a customer service application, a consumer web portal application, and an integrated voice response application.

11. The method of claim 8 further comprising:
decomposing the reusable service into one or more additional reusable services for getting the member's coverage eligibility status, getting the member's health insurance claim detail, and finding one or more other members related to the member.

12. The method of claim 11 wherein the reusable service for finding one or more other members related to the member includes multiple levels of granularity by accepting input of one or more of member's name, zip code, and address.

13. The method of claim 8 wherein the reusable service comprises a service for retrieving a health insurance plan member's health plan benefit information.

14. The method of claim 13 further comprising decomposing the reusable service into one or more reusable services for identifying the member, obtaining health plan sponsor information, obtaining health plan sponsor entitlement information, obtaining health plan details, obtaining member coverage eligibility, and obtaining history of member coverage eligibility updates.

15. In a service oriented architecture for a health care enterprise computer system, a non-transitory computer readable medium having stored thereon computer executable instructions for providing a reusable service to a plurality of health care applications, the instructions comprising:
receiving a service request from at least one of the plurality of health care applications;
parsing the service request to identify one or more of user identification fields, requested data fields, and requested action fields;
dynamically customizing the reusable service for the at least one of the plurality of health care applications based on one or more of the parsed service request fields;
invoking the customized reusable service; and
communicating a result from the customized reusable service to at least one of the plurality of health care applications,
wherein the reusable service comprises a service for retrieving health insurance plan member information, the instructions further comprising decomposing the reusable service into one or more additional reusable services for getting the member's coverage eligibility status, getting the member's health insurance claim detail, and finding one or more other members related to the member.

16. The computer readable medium of claim 15 wherein the reusable service for finding one or more other members related to the member includes multiple levels of granularity by accepting input of one or more of member's name, zip code, and address.

17. The computer readable medium of claim 15 wherein the reusable service comprises a service for retrieving health insurance plan member's health plan benefit information, the instructions further comprising decomposing the reusable service into one or more reusable services for identifying the member, getting health plan sponsor information, getting health plan sponsor entitlement information, getting health plan details, getting member coverage eligibility, and getting history of member coverage eligibility updates.

* * * * *